United States Patent [19]

Orban et al.

[11] Patent Number: 4,683,326
[45] Date of Patent: Jul. 28, 1987

[54] SOLVENT-FREE CRYSTALLIZATION OF PENTAERYTHRITOL TETRAKIS-[3-(3,5-DI-TERT-BUTYL-4-HYDROXYPHENYL)PROPIONATE] AND THE NOVEL ALPHA-CRYSTALLINE FORM THEREOF

[75] Inventors: Ivan Orban; Werner Fussenegger, both of Basel, Switzerland

[73] Assignee: Ciba-Geigy Corporation, Ardsley, N.Y.

[21] Appl. No.: 884,254

[22] Filed: Jul. 10, 1986

[30] Foreign Application Priority Data

Jul. 19, 1985 [CH] Switzerland ................ 3146185

[51] Int. Cl.$^4$ .............................. C07C 69/76
[52] U.S. Cl. ............................................ 560/75
[58] Field of Search .................................. 560/75

[56] References Cited

U.S. PATENT DOCUMENTS 4,085,132  4/1978  Park ........................... 560/75

FOREIGN PATENT DOCUMENTS 288839   4/1967  Australia ..................... 560/75
1177092  10/1984 Canada ........................ 560/75
9025349  9/1984  Japan ......................... 560/75

Primary Examiner—Paul J. Killos
Attorney, Agent, or Firm—Harry Falber

[57] ABSTRACT

Seeding a melt of pentaerythritol tetrakis-[3-(3,5-di-tert-butyl-4-hydroxyphenyl)propionate] with a small amount of the crystalline $\beta$-, $\delta$- or $\lambda$-modification of this compound in an extruder, kneader or internal mixer at 70°–130° C. gives, within a few minutes, pure crystalline product without the use of a hitherto mandatory and environmentally undesirable solvent.

Also described is a novel crystalline thermostable $\lambda$-modification of pentaerythritol tetrakis-[3-(3,5-di-tert-butyl-4-hydroxyphenyl)propionate].

11 Claims, No Drawings

SOLVENT-FREE CRYSTALLIZATION OF PENTAERYTHRITOL TETRAKIS-[3-(3,5-DI-TERT-BUTYL-4-HYDROXYPHENYL)PROPIONATE] AND THE NOVEL ALPHA-CRYSTALLINE FORM THEREOF

The present invention relates to a process for the complete, solvent-free crystallisation of pentaerythritol tetrakis-[3-(3,5-di-tert-butyl-4-hydroxyphenyl)propionate] and to a novel crystalline form (λ-modification) of this compound.

Pentaerythritol tetrakis-[3-(3,5-di-tert-butyl-4-hydroxyphenyl)propionate], which is prepared by methods known per se such as those described e.g. in U.S. Pat. Nos. 3,644,482, 4,228,297 and 4,405,807, and which has long been known and commercially available as an excellent antioxidant for organic material, has up to now had to be recrystallised from an organic solvent for it to be obtained in a crystalline form sufficiently pure to meet technical requirements.

It is also known that almost quantitatively pure pentaerythritol tetrakis-[3-(3,5-di-tert-butyl-4-hydroxyphenyl)propionate] is obtained by transesterification of methyl 3-(3,5-di-tert-butyl-4-hydroxyphenyl)propionate with pentaerythritol in the presence of a catalytic amount of an oxide or of an organometal compound of metals of the fourth main or auxiliary group of the Periodic Table, and subsequent distillation of the resultant melt in a flash distillation apparatus under vacuum and at elevated temperature, i.e. without the use of a solvent. The solidified product melt obtained after cooling is then comminuted. However, this product is amorphous and melts at 55°–62° C. For reasons of storage and transportion stability alone, however, a crystalline structure of higher melting point would be a considerable advantage over the amorphous form.

For technical and economic reasons, but especially for environmental reasons, crystallisation of the product without using a solvent would be desirable. One possibility of avoiding the use of a solvent consists in the use of melt crystallisation. So far it has not been known to obtain the product by such a crystallisation method. Attempts to do so have failed up to now, as the melt of pentaerythritol tetrakis-[3-(3,5-di-tert-butyl-4-hydroxyphenyl)propionate] crystallises extremely poorly. Attempts to crystallise the melt normally result in mixtures of crystalline and amorphous products. The amorphous products, however, are highly undesirable. Even in small amounts they induce a green or yellow discolouration of the basically colourless product under the action of light. Thus, for example, the granulation of a melt/crystalline suspension on a cooling belt or in a spray tower always results in a partially amorphous and therefore unsuitable granular formulation.

There is consequently a need to convert pentaerythritol tetrakis-[3-(3,5-di-tert-butyl-4-hydroxyphenyl)propionate], without a solvent, direct and completely into crystalline form by means of a process that is suitable for large-scale production. Surprisingly, it has now been found that such a complete crystallisation is possible direct from the melt by seeding said melt, under specific conditions, in an extruder, a kneader or an internal mixer with specific crystalline forms of the product.

Accordingly, the present invention relates to a process for the complete, solvent-free crystallisation of pentaerythritol tetrakis-[3-(3,5-di-tert-butyl-4-hydroxyphenyl)propionate], which comprises seeding a melt of this compound in an extruder, a kneader or an internal mixer with at least 0.1 to 5% by weight, based on said melt, of the β-, δ- or λ-crystal modification of said compound, at a temperature in the range from 70° to 130° C.

As melt for the crystallisation, it is especially preferred to use the melt obtained direct from the transesterification of methyl 3-(3,5-di-tert-butyl-4-hydroxyphenyl)propionate with pentaerythritol.

The process of this invention is carried out in the apparatus commonly known and employed in process technology as extruders, kneaders and internal mixers. It is preferred to use an extruder, for example a single-screw or double-screw extruder or a planetary roller extruder. If an extruder or internal mixer is employed, the process is preferably carried out continuously, whereas in a kneader it is preferably carried out batchwise.

The known β- or δ-crystal modifications of pentaerythritol tetrakis-[3-(3,5-di-tert-butyl-4-hydroxyphenyl)propionate] may be used for seeding the melt; but the use of the novel λ-modification described hereinafter is preferred. When using seed crystals of the β-modification in the process of the invention, the product is likewise obtained in the β-modification and, when using seed crystals of the δ- and λ-modification, the crystallised product is obtained in each case in the λ-modification.

It is preferred to add the seed crystals in an amount, based on the melt, of 0.1 to 3, in particular of 0.1 to 2, e.g. 0.8 to 1.2 and, most preferably, about 1% by weight. The seed crystals can, of course, also be added in an amount of more than 5% without any diminution in the quality or yield of the crystallised product. However, larger amounts are uneconomical and therefore not used in practice.

A preferred embodiment is that which comprises seeding the melt obtained from the transesterification of methyl 3-(3,5-di-tert-butyl-4-hydroxyphenyl)propionate with pentaerythritol at 70°–130° C. with 0.5 to 5% by weight of the λ-crystal modification of pentaerythritol tetrakis-[3-(3,5-di-tert-butyl-4-hydroxyphenyl)propionate].

The preferred temperature range in which the process of the invention is carried out is from 70° C. to the melting point of the respective mixed crystals employed or of the mixture consisting of melt and mixed crystals. Examples of temperature ranges which may be employed in practice are from 80° C., preferably 90° C., to the melting point of the respective mixed crystals. At all events, a temperature must be chosen at which the seed crystals do not melt completely during the residence time in the apparatus. A preferred temperature range is from 90° to 110° C., most preferably from 95° to 105° C., e.g. 100° C.

The crystallisation of the melt can take place very rapidly and thus economically. When using an extruder, residence times of e.g. 3–5 minutes are possible in practice.

In general, the residence time (crystallisation time) also depends on whether the process is carried out batchwise or continuously. It may be for example from 1 to 30, preferably from 2 to 20 and, most preferably, from 2 to 10 minutes.

A 100% crystallisation of the melt is obtained by the process of this invention, i.e. no amorphous product is formed. The resultant granulate meets stringent quality requirements, as it is stable to light. If the melt were seeded with the seed crystals e.g. in a laboratory stirring apparatus, the melt would crystallise but it would have to be stirred for about 1 hour or longer, and the product would still contain at least 1–3% of amorphous product and so not conform to the exacting requirements of actual practice.

The present invention further relates to a novel crystal modification (λ-modification) of pentaerythritol tetrakis-[3-(3,5-di-tert-butyl-4-hydroxyphenyl)propionate], characterised by an X-ray diffraction pattern which exhibits lines of very high intensity at an interplanar spacing of 5.24, 8.4 and 12.4 Å, lines of strong intensity at an interplanar spacing of 4.62, 6.3, 6.6, 6.7, 7.2 and 13.3 Å, lines of medium intensity at an interplanar spacing of 3.78, 3.99, 4.14, 4.22, 4.25, 4.35, 4.44, 4.74, 4.84, 4.98, 5.06, 5.63, 6.0, 9.2 and 11.7 Å, and lines of weak intensity at an interplanar spacing of 3.38, 3.43, 3.72, 3.82, 4.03, 4.40, 4.79, 5.52, 7.0, 10.0, 12.2 and 17.7 Å.

It has been found that this novel λ-modification can be obtained by thermal treatment from the thermodynamically unstable δ-modification known from U.S. Pat. No. 4,405,807.

The present invention hence also relates to a process for the preparation of the above described λ-modification, which comprises heating a melt of pentaerythritol tetrakis-[3-(3,5-di-tert-butyl-4-hydroxyphenyl)propionate] which contains δ-crystals of this compound, while mixing thoroughly, to a temperature in the range from 90° C. to the melting point of the system consisting of melt/δ-crystals.

The novel λ-modification has a melting point of about 124° C., compared with 118° C. of the δ-modification and about 116° C. of the β-modification.

The concentration of δ-crystals in the melt is not crucial and may for example have the values cited above for the melt crystallisation process of this invention.

The temperature range for the preparation of the novel λ-modification is e.g. 90°–115° C., preferably 95°–115° C. and, most preferably, 100°–110° C. The melt is preferably stirred at the transition temperature so as to obtain as substantial a conversion as possible, for some time, e.g. from ½ hour to 10 hours, e.g. 1 to 5 hours. If the conversion is carried out in conventional laboratory apparatus, the conversion is incomplete, as amorphous product is formed (see above). This simple process, however, can be utilised to produce λ-seed crystals for the melt crystallisation of the invention. Naturally, the λ-crystals can also be obtained direct by the melt crystallisation if seed crystals of the δ-modification are used therein. In practice, seed crystals will of course in that case be recycled from the crop of λ-crystals to the crystallisation apparatus. Thus a start is made e.g. with δ-seed crystals and then some of the resultant (e.g. extruded) crop of λ-crystals are fed back continuously into the process.

The thermodynamically stable novel λ-crystal modification of pentaerythritol tetrakis-[3-(3,5-di-tert-butyl-4-hydroxyphenyl)propionate] is a preferred modification of this compound which has a number of different advantages compared with other modifications. For example, the use of λ-crystals as seed crystals in the melt crystallisation process of this invention is particularly preferred, as the crystallisation proceeds especially rapidly and completely therewith. Further, the λ-modification has a higher melting point than the known β- and δ-modifications—an advantage as regards transportation and storage stability.

The invention is illustrated in more detail by the following non-limitative Examples.

EXAMPLE 1

Preparation of λ-seed crystals 1000 g of pentaerythritol tetrakis-[3-(3,5-di-tert-butyl-4-hydroxyphenyl)propionate] in the δ-form (m.p. 114°–116° C.) are heated to 130° C. in a flask to form a clear melt. This melt is cooled to 105° C. and mixed with 10 g of pentaerythritol tetrakis-[3-(3,5-di-tert-butyl-4-hydroxyphenyl)propionate] in the δ-form. The suspension is stirred at c. 105° C. Crystallisation commences after about 2 to 3 hours. The temperature in the flask rises and must be kept below 115° C. by external cooling. The suspension becomes increasingly dense and finally congeals to a hard crystalline solid, which is comminuted after cooling. Crystals of the λ-modification are confirmed by X-ray analysis. Differential thermoanalysis indicates the presence of 1 to 3% of amorphous product with a melting point of 55°–60° C. in addition to the main product with a melting point of 122°–123° C. (λ).

EXAMPLE 2

Crystallisation of the melt by seeding with λ-seed crystals

A melt of pentaerythritol tetrakis-[3-(3,5-di-tert-butyl-4-hydroxyphenyl)propionate] is fed from a storage vessel at a temperature of 100°–105° C. to a pilot planetary roller extruder (without die) at a rate of 5 kg/h and at a screw speed of 20 rpm. The extruder is uniformly heated to 90° C. Simultaneously, crystals of the λ-modification of pentaerythritol tetrakis-[3-(3,5-di-tert-butyl-4-hydroxyphenyl)propionate] (obtained by the method described in Example 1) are fed by means of a metering screw at a rate of c. 0.05 kg/h (corresponding to a concentration of c. 1% by weight, based on the melt) to the melt being fed to the extruder. The temperature of the product in the extruder rises to a maximum of 110° C., and then falls again. The product, which is obtained in the form of coarse, hard lumps, is subsequently comminuted. It is homogeneous and consists of crystals of the λ-modification. Differential thermoanalysis shows that no amorphous product is present. Melting point: 124° C.

In the further course of the extruder crystallisation, some of the product is, of course, recycled in the form of seed crystals to the process. In practice, the melt obtained direct from the transesterification of methyl 3-(3,5-di-tert-butyl-4-hydroxyphenyl)propionate with pentaerythritol is used as crystallisation melt.

EXAMPLE 3

The procedure of Example 2 is repeated, except that 0.065 kg/h of crystals of the δ-modification of pentaerythritol tetrakis-[3-(3,5-di-tert-butyl-4-hydroxyphenyl)propionate] with a melting point of 112°–118° C. (corresponding to a concentration of c. 1.3% by weight, based on the melt) is fed to the extruder by means of a metering screw instead of 0.05 kg/h of the λ-modification. The temperature in the extruder then rises to a maximum of 114° C. A homogeneous product consisting of λ-crystals with a melting point of 124° C. is likewise obtained.

EXAMPLE 4

The procedure of Example 2 is repeated, except that 0.035 kg/h of crystals of the β-modification of pentaerythritol tetrakis-[3-(3,5-di-tert-butyl-4-hydroxyphenyl)propionate] with a melting point of 111°–116° C. (corresponding to a concentration of c. 0.7% by weight, based on the melt) is fed to the extruder by means of a metering screw instead of 0.05 kg/h of the λ-modification. The temperature in the extruder then rises to a maximum of 105° C. A homogeneous product consisting of β-crystals with a melting point of 116° C. is obtained.

What is claimed is:

1. A process for the complete, solvent-free crystallisation of pentaerythritol tetrakis-[3-(3,5-di-tert-butyl-4-hydroxyphenyl)propionate], which comprises seeding a melt of this compound in an extruder, a kneader or an internal mixer with at least 0.1 to 5% by weight, based on said melt, of the β-, δ- or λ-crystal modification of said compound, at a temperature in the range from 70° to 130° C.

2. A process according to claim 1, which comprises using the melt obtained direct from the transesterification of methyl 3-(3,5-di-tert-butyl-4-hydroxyphenyl)propionate with pentaerythritol as crystallisation melt.

3. A process according to claim 1 which is carried out in an extruder.

4. A process according to claim 3 which is carried out continuously.

5. A process according to claim 1, wherein the melt is seeded with crystals of the λ-modification.

6. A process according to claim 1, wherein the seed crystals are used in an amount of 0.1 to 2, preferably of 0.8 to 1.2% by weight, based on the melt.

7. A process according to claim 1, which comprises seeding the melt obtained from the transesterification of methyl 3-(3,5-di-tert-butyl-4-hydroxyphenyl)propionate with pentaerythritol at 70°–130° C. with 0.5 to 5% by weight, based on the melt, of the λ-crystal modification of pentaerythritol tetrakis-[3-(3,5-di-tert-butyl-4-hydroxyphenyl)propionate].

8. A process according to claim 1, wherein crystallisation is carried out at a temperature in the range from 70° C. to the melt temperature of the respective seed crystals.

9. A process according to claim 8, wherein crystallisation is carried out in the temperature range from 90°–110° C.

10. The λ-modification of pentaerythritol tetrakis-[3-(3,5-di-tert-butyl-4-hydroxyphenyl)propionate], characterised by an X-ray diffraction pattern which exhibits lines of very high intensity at an interplanar spacing of 5.24, 8.4 and 12.4 Å, lines of strong intensity at an interplanar spacing of 4.62, 6.3, 6.6, 6.7, 7.2 and 13.3 Å, lines of medium intensity at an interplanar spacing of 3.78, 3.99, 4.14, 4.22, 4.25, 4.35, 4.44, 4.74, 4.84, 4.98, 5.06, 5.63, 6.0, 9.2 and 11.7 Å, and lines of weak intensity at an interplanar spacing of 3.38, 3.43, 3.72, 3.82, 4.03, 4.40, 4.79, 5.52, 7.0, 10.0, 12.2 and 17.7 Å.

11. A process for the preparation of the λ-modification according to claim 10, which comprises heating a melt of pentaerythritol tetrakis-[3-(3,5-di-tert-butyl-4-hydroxyphenyl)propionate] which contains δ-crystals of this compound, while mixing thoroughly, to a temperature in the range from 90° C. to the melting point of the system consisting of melt/δ-crystals.

* * * * *